US008808162B2

(12) United States Patent
Gindele et al.

(10) Patent No.: US 8,808,162 B2
(45) Date of Patent: Aug. 19, 2014

(54) IMPLANTS, TOOLS, AND METHODS FOR TREATMENT OF PELVIC CONDITIONS

(75) Inventors: Paul J. Gindele, Minnetonka, MN (US); Justin M. Crank, Minnetonka, MN (US); Matthew S. Finlay, Minnetonka, MN (US); William J. Rissmann, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 168 days.

(21) Appl. No.: 13/432,632

(22) Filed: Mar. 28, 2012

(65) Prior Publication Data

US 2012/0253107 A1   Oct. 4, 2012

Related U.S. Application Data

(60) Provisional application No. 61/468,096, filed on Mar. 28, 2011, provisional application No. 61/496,125, filed on Jun. 13, 2011.

(51) Int. Cl.
*A61F 2/00* (2006.01)

(52) U.S. Cl.
USPC .............................................. 600/37; 600/30

(58) Field of Classification Search
USPC ................................................ 600/29–31, 37
See application file for complete search history.

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,613,679 A | 10/1971 | Bijou |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

Studdiford, William E., Transplantation of Abdominal Fascia for the Relief of Urinary Stress Incontinence, American Journal of Obstetrics and Gynecology, pp. 764-775 (1944).

(Continued)

*Primary Examiner* — John Lacyk
(74) *Attorney, Agent, or Firm* — Kagan Binder, PLLC

(57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to supportive tissue and adjusting the implant.

19 Claims, 7 Drawing Sheets

(56) References Cited

U.S. PATENT DOCUMENTS

| | | |
|---|---|---|
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Velaquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,732,475 A | 3/1998 | Sacks et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,142,968 A | 11/2000 | Pigg et al. |
| 6,168,611 B1 | 1/2001 | Rizvi |
| 6,174,279 B1 | 1/2001 | Girard |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,432,074 B1 | 8/2002 | Ager et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |

(56) References Cited

U.S. PATENT DOCUMENTS

| | | |
|---|---|---|
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,682,475 B2 | 1/2004 | Cox et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski et al. |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,226,407 B2 | 6/2007 | Kammerer et al. |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,285,103 B2 | 10/2007 | Nathanson |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosley et al. |
| 7,789,821 B2 | 9/2010 | Browning |
| 8,172,745 B2 | 5/2012 | Rosenblatt |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0053903 A1 | 3/2006 | Berenyi et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0028828 A1 | 7/2006 | Cox et al. |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078275 A1 | 4/2007 | Landgrebe |
| 2007/0162120 A1* | 7/2007 | Bouffier ................... 623/11.11 |
| 2007/0173864 A1 | 7/2007 | Chu |
| 2008/0039678 A1 | 2/2008 | Montpetit et al. |
| 2008/0072404 A1 | 3/2008 | Wetter |
| 2008/0251002 A1 | 10/2008 | Burleigh |
| 2008/0300607 A1 | 12/2008 | Meade et al. |
| 2009/0005634 A1 | 1/2009 | Rane |
| 2009/0012353 A1 | 1/2009 | Beyer |
| 2009/0192346 A1* | 7/2009 | Rosenblatt ................... 600/30 |
| 2009/0221868 A1 | 9/2009 | Evans |
| 2010/0261950 A1 | 10/2010 | Lund et al. |
| 2011/0124954 A1 | 5/2011 | Ogdahl et al. |
| 2011/0297161 A1* | 12/2011 | Deitch ................... 128/834 |

(56) References Cited

U.S. PATENT DOCUMENTS

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 223297 A * | 4/1989 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 4/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2005037132 A2 | 4/2005 |
| WO | WO2005079702 A2 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007/149555 * | 12/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J, vol. 12, pp. 187-192 (2001).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): an Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).
UroMed Access Instrument System for the Sub-urethral Sling Procedure Catalog No. 120235, Directions for Use, (3 pages).
Vesica® Percutaneous Bladder Neck Stabilization Kit, A New Approach to Bladder Neck Suspenison, Microvasive® Boston Scientific Corporation, 4 pages (1995).
Vesica® Sling Kits, Simplifying Sling Procedures, Microvasive® Boston Scientific Corporation, 4 pages (1998).
Villet, R., Réponse De R. Villet Á L'Article De D. Dargent et al., Gynécolgie Obstétrique & Fertilité, vol. 31, p. 96 (2003).

(56) References Cited

OTHER PUBLICATIONS

Visco, Anthony G. et al., Vaginal Mesh Erosion After Abdominal Sacral Colpopexy, Am J Obstet Gynecol, vol. 184, n. 3, pp. 297-302 (297-302).
Walters, Mark D., Percutaneous Suburethral Slings: State of the Art, Presented at the conference of the American Urogynecologic Society, Chicago, 29 pages (Oct. 2001).
Waxman, Steve et al., Advanced Urologic Surgery for Urinary Incontinence, The Female Patient, pp. 93-100, vol. 21 (Mar. 1996).
Weber, Anne M. et al., Anterior Vaginal Prolapse: Review of Anatomy and Techniques of Surgical Repair, Obstetrics and Gynecology. vol. 89, n. 2, pp. 311-318 (Feb. 1997).
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B. Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology and Nephrology. Supplement 153: p. 1 (1993).
Horbach, Nicollette, Suburethral Sling Procedures, Genuine Stress Incontinence, Chapter 42, pp. 569-579.
Mentor Porges, Uratape, ICS/IUGA Symp, Jul. 2002.
"We're staying ahead of the curve" Introducing the IVS Tunneller Device for Tension Free Procedures, Tyco Healthcare, 3 pages (2002).
Advantage A/T™, Surgical Mesh Sling Kit, Boston Scientific, 6 pages (2002).
Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).
Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).
Araki, Tohru et al., The Loop-Loosening Procedure for Urination Difficulties After Stamey Suspension of the Vesical Neck, The Journal of Urology, vol. 144, pp. 319-323 (Aug. 1990).
Asmussen, M. et.al., Simultaneous Urethro-Cystometry With a New Technique, Scand J Urol Nephrol 10, pp. 7-11 (1976).
Beck, Peter R. et al., Treatment of Urinary Stress Incontinence With Anterior Colporrhaphy, Obstetrics and Gynecology. vol. 59 (No. 3), pp. 269-74 (Mar. 1982).

Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology. vol. 145, pp. 1214-1218 (Jun. 1991)
Blaivas, Jerry et al., Type III Stress Urinary Incontinence: Importance of Proper Diagnosis and Treatment, Surgical Forum, pp. 473-475, (1984).
Blaivas, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation With Cooper's Ligament Attachment in the Management of Recurrent Urinary Stress Incontinence, American Journal of Obstetrics and Gynecology. vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn, vol. 31, pp. 281-290 (1961).
Capio™ CL—Transvaginal Suture Capturing Device—Transvaginal Suture Fixation to Cooper's Ligament for Sling Procedures, Boston Scientific, Microvasive®, 8 pages, (2002).
Cervigni, Mauro et al., the Use of Synthetics in the Treatment of Pelvic Organ Prolapse, Voiding Dysfunction and Female Urology, vol. 11, pp. 429-435 (2001).
Choe, Jong M. et al., Gore-Tex Patch Sling: 7 Years Later, Urology, vol. 54, pp. 641-646 (1999).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodinance, Philipp et al., "Tolerance of Synthetic Tissues in Touch With Vaginal Scars: Review to the Point of 287 Cases", European Journal of Obstetrics & Gynecology and Reproductive Biology 87 (1999) pp. 23-30.
Decter, Ross M., Use of the Fascial Sling for Neurogenic Incontinence: Lessons Learned, The Journal of Urology, vol. 150, pp. 683-686 (Aug. 1993).
Delancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).
Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).
Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pages 45-50 (1990).
Falconer, C. et al., Clinical Outcome and Changes in Connective Tissue Metabolism After Intravaginal Slingplasty in Stress Incontinence Women, International Urogynecology Journal, pp. 133-137 (1966).

(56) References Cited

OTHER PUBLICATIONS

Falconer, C. et al., Influence of Different Sling Materials of Connective Tissue Metabolism in Stress Urinary Incontinent Women, International Urogynecology Journal, Supp. 2, pp. S19-S23 (2001).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide,6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101, n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).
Hodgkinson. C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H. et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Obstet., vol. 10, pp. 51-69 (1983).
IVS Tunneller—A Universal instrument for anterior and posterior intra-vaginal tape placement, Tyco Healthcare, 4 pages (Aug. 2002).
IVS Tunneller—ein universelles Instrument fur die Intra Vaginal Schlingenplastik, Tyco Healthcare, 4 pages. (2001).
Jeffcoate. T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontintence, British Journal of Obstetrics and Gynaecology. vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).
Korda, A. et al., Experience With Silastic Slings for Female Urinary Incontinence, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kovac, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).
Leach, Gary E., MD, Bone Fixation Technique for Transvaginal Needle Suspension, Urology Vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).
Marchionni, Mauro et al., True Incidence of Vaginal Vault Prolapse—Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at the University of Michigan, Journal of Urology, vol. 138, pp. 90-93(1987).
McGuire, Edwared J. et al., Abdominal Fascial Slings, Slings, Raz Female Urology, p. 369-375(1996).
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).

(56) References Cited

OTHER PUBLICATIONS

McKiel, Charles F. Jr., et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., A Simplified Sling Operation Suitable for Routine Use, Gynecological and Obstetrical Clinic, University of Vienna, vol. 84, No. 3, p. 400-405, (Aug. 1, 1962).
Natale, F. et al., Tension Free Cystocele Repair (TCR): Long-Term Follow-Up, International Urogynecology Journal, vol. 11, supp. 1, p. S51 (Oct. 2000).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N. Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and Mcguire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology. vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).
Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa at al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics. Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics. Sup 153, p. 73-75 (1993).
Petros, Peter E. Papa et al., The Further Development of the Intravaginal Slingplasty Procedure—IVS V —(With "Double Breasted" Unattached Vaginal Flap Repair and Permanent Sling)., Scandinavian Journal of Neurourology and Urodynamics. Sup 153, pp. 77-79 (1993).
Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp, 453-461 (1996).

(56) References Cited

OTHER PUBLICATIONS

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics. Sup 153, pp. 81-84 (1993).

Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).

Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).

Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).

Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).

Petros. Peter E. Papa, Development of Generic Models for Ambulatory Vaginal Surgery—Preliminary Report, International Urogynecology Journal, pp. 20-27 (1998).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).

Petros, Peter E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).

Rackley, Raymond R. et al., Tension-Free Vaginal Tape and Percutaneous Vaginal Tape Sling Procedures, Techniques in Urology, vol. 7, No. 2, pp. 90-100 (2001).

Rackley, Raymond R. M.D., Synthetic Slings: Five Steps for Successful Placement, Urology Times, p. 46,48,49 (Jun. 2000).

Raz, Shlomo, et al., The Raz Bladder Neck Suspension Results in 206 Patients, The Journal of Urology, pp. 845-46 (1992).

Raz, Shlomo, Female Urology, pp. 80-86, 369-398, 435-442 (1996).

Raz, Shlomo, MD, Modified Bladder Neck Suspension for Female Stress Incontinence, Urology, vol. XVII, No. 1, pp. 82-85 (Jan. 1981).

Richardson, David A. et al., Delayed Reaction to the Dacron Buttress Used in Urethropexy, The Journal of Reproductive Medicine, pp. 689-692. vol. 29, No. 9 (Sep. 1984).

Richter, K., Massive Eversion of the Vagina: Pathogenesis, D Agnosis and Therapy of the "True" Prolapse of the Vaginal Stump, Clin obstet gynecol, vol. 25, pp. 897-912 (1982).

Ridley, John H., Appraisal of the Goebell-Frangenheim-Stoeckel Sling Procedure, American Journal Obst & Gynec., vol. 95, No. 5, pp. 741-721 (Jul. 1, 1986).

Roberts, Henry, M.D., Cystourethrography in Women, Deptment of Obstetrics and Gynaecology, University of Liverpool, May 1952, vol. XXXV, No. 293, pp. 253-259.

Sabre™ Bioabsorbable Sling, Generation Now, Mentor, 4 pages (May 2002).

Sabre™ Surgical Procedure, Mentor, 6 pages (Aug. 2002).

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Seim, Arnfinn et al., A Study of Female Urinary Incontinence in General Practice—Demography, Medical History, and Clinical Findings, Scand J Urol Nephrol, vol. 30, pp. 465-472 (1996).

Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).

Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).

Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).

Stamey, Thomas A., M.D., Endoscopic Suspension of the Vesical Neck for Urinary Incontinence in Females, Ann. Surgery, vol. 192 No. 4, pp. 465-471 (Oct. 1980).

Stanton, Stuart L., Suprapubic Approaches for Stress Incontinence in Women, Journal of American Geriatrics Society, vol. 38, No. 3, pp. 348-351 (Mar. 1990).

Stanton, Stuart, Springer-Veglag, Surgery of Female Incontinence, pp. 105-113 (1986).

Staskin, David R. et al., The Gore-Tex Sling Procedure for Female Sphincteric Incontinence: Indications, Technique, and Results, World Journal of Urology, vol. 15, pp. 295-299 (1997).

* cited by examiner

IMPLANTS, TOOLS, AND METHODS FOR TREATMENT OF PELVIC CONDITIONS

PRIORITY CLAIM

The present non-provisional patent Application claims priority under 35 USC §119(e) from U.S. Provisional Patent Application having Ser. No. 61/468,069, filed Mar. 28, 2011, entitled "IMPLANTS, TOOLS, AND METHODS FOR TREATMENTS OF PELVIC CONDITIONS," and U.S. Provisional Patent Application having Ser. No. 61/496,125, filed Jun. 13, 2011, entitled "IMPLANTS, TOOLS, AND METHODS FOR TREATMENTS OF PELVIC CONDITIONS," both of which are hereby incorporated by reference in their entireties.

FIELD OF THE INVENTION

The present invention relates generally to implants, tools, devices, systems, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Tension of an implant is typically adjusted during an implantation procedure sufficiently to take up any slack in the sling and impart at least a degree of increased and efficacious tension or desired positioning of supported tissue. Typically, implants such as urethral tapes or slings are fabricated of a loose weave sling fabric or mesh that engages tissue and encourages tissue ingrowth along the pathway through mesh pores to achieve chronic stabilization or "self-fixation." Tissue ingrowth can take about 2-3 weeks in a typical patient in the absence of any significant intentional or unintentional movement of the mesh. During this post-operative time, the patient monitors the degree of success achieved in ameliorating symptoms of incontinence (e.g., urinary leakage) and any discomfort that might occur if the applied tension is so high as to unduly slow voluntary urination (for treating urinary incontinence). If any such problems occur it may be necessary to reopen the original surgical incisions to access and pull on the implant ends to tighten the central portion around the urethra (or other tissue being supported) or to on the implant central support portion to loosen the central support portion around the urethra. Several approaches have been taken to simplify or reduce the need for such post-operative adjustments.

Although effective in alleviating incontinence (e.g., anal, SUI), improvements in urethral and anal slings and other pelvic floor implants to post-operatively adjust tension applied to the urethra, anus, or other pelvic floor tissue, are desirable.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies, and the like.

Described devices and methods involve improvements in pelvic implants, including elongated incontinence slings that include a central support portion and end portions extending from the central portion to sling ends. Herein, the terms "sling," "implant," and "incontinence sling" without further qualification are used interchangeably to include various forms of pelvic implants for supporting different pelvic tissues, and specifically include urethral slings adapted to be placed through a tissue pathway in a male or female patient, disposing the central support portion below the urethra or bladder neck (hereafter collectively referred to as the urethra for convenience) (and above the vaginal wall in a female patient) to alleviate urinary incontinence, and fecal slings adapted to be placed through a tissue pathway disposing the central support portion inferior to the anus, the anal sphincter, or the lower rectum (hereafter collectively referred to as the anus for convenience) to alleviate fecal incontinence.

In accordance with the present description, such slings are improved to enhance post-operative sling adjustment of the tension applied to the urethra, anus, or other supported tissue, to enhance efficacy of the implant and method of treatment, and for improved patient comfort. Various specific embodiments of the implants and methods are described herein. The various embodiments are applicable to both male and female patients to address issues of incontinence in both, to address issues of prolapse repair in female patients, and to address perineal floor descent and fecal incontinence in both. Also, surgical techniques such as forming suprapubic, retropubic, transobturator, "inside-out" and "outside-in" tissue pathways between two incisions, or a tissue pathway formed from a single incision through the vagina or perineal floor (in male or female patients) are also contemplated for passage of a sling therethrough.

In various embodiments, one or two sling tension adjusting mechanisms can be located at distal ends of extension portions of a sling. In use, the adjusting mechanisms, preferably two adjusting mechanisms located at opposed ends of an implant, can be implanted in a patient at a locate near a skin surface for improved post-surgical access. With the implant installed to support tissue, the adjusting mechanisms can be sufficiently close to a skin surface to allow post-operative engagement, communication with, or actuation of the adjusting mechanism. In certain embodiments, the post-operative communication can be performed by opening or re-opening an incision in the skin adjacent to a subcutaneously-implanted adjusting mechanism, to allow direct contact with the subcutaneously-implanted adjusting mechanism through the incision in the skin. In other embodiments the post-operative communication can be performed through the intact skin tissue without opening or re-opening an incision in the skin; in these embodiments, the subcutaneously-implanted adjusting mechanism can be controlled by an external adjustment tool that communicates with the adjusting mechanism through the intact skin, to actuate the adjusting mechanism to tighten or loosen the implant within the patient.

Various adjustment tools and techniques can be used to actuate the adjusting mechanisms to decrease or increase the length of a sling end portion and to thereby increase or decrease, respectively, the tension applied by the central support portion to supported tissue (e.g., the urethra or anus). Adjusting mechanisms are disposed at distal ends of the end portions and can be placed subcutaneously so as to be disposed sufficiently near the patient's skin to enable application of an adjustment tool against the skin or through the skin and underlying tissues to operate the adjusting mechanisms.

According to certain embodiments, an external adjustment tool can be used to communicate with and actuate an adjusting mechanism through intact skin tissue, without creating an incision in the skin. The adjustment tool can include a signal transmitter capable of generating an adjustment command that passes transcutaneously (through the intact skin), and the adjusting mechanism includes a receiver for receiving the transmitted commands. An adjusting mechanism of such an implant can be manipulated post-operatively without invasive means by using the external adjustment tool transcutaneously to activate the adjusting mechanism. The external adjustment tool can include a mechanical, magnetic, or electromagnetic coupling that communicates with the internal adjusting mechanism, and the external adjustment tool can be used to activate the internal adjusting mechanism to add or reduce the tension on a component of the implant.

In certain embodiments an external adjustment tool can alternately or additionally include a magnetic field generator or permanent magnet that can be used to generate a magnetic field representing a sling adjustment command that passes transcutaneously through the skin, and the adjusting mechanism includes a magnetic field-responsive element that responds to the magnetic field of the external adjustment tool.

In yet alternate embodiments an external adjustment tool can alternately or additionally include a frictional engagement that can be used to engage a complementary engagement surface of the adjusting mechanism, transcutaneously, through intact skin.

In still another embodiment, the adjustment tool is used by inserting a portion of the adjustment tool percutaneously (penetrating the skin) to engage and operate the adjusting mechanism. An adjustment tool can actuate the adjustment tool by any mode, such as by a mechanical engagement, magnetic engagement, an electromechanical mechanism, or the like.

According to preferred devices and methods, an implant can include two adjusting mechanisms, one at each of two opposing ends of an implant. The use of two adjusting mechanisms on opposite sides of the implant (and patient) allows the implant to be adjusted in a balanced fashion that prevents supported tissue from being pulled to one side or the other upon adjustment. Devices and methods that involve two adjusting mechanisms allow the implant to be adjusted on both sides, thereby allowing the implant to be adjusted to not just increase tension, but to increase tension and simultaneously adjust the position of (approximate) the tissue being supported exclusively along a medial axis of the patient; in other words, the tissue being supported is not pulled in a left or a right direction relative to a midline of the patient during adjustment but remains in an anatomically correct manner at a location on the midline.

The adjusting mechanisms can be used in situations where the location or tension on an implant is desirably revised or adjusted after implantation, post-surgically, such as if the patient is in retention or if the results achieved by the surgical procedure are not satisfactory. Such tension adjustment procedure can advantageously be performed immediately after surgery (e.g., within 1 or 2 hours) or at a later time such as during recovery from original surgery (e.g., within 1, 2, or 3 days or within 1, 2, or 3 weeks).

In one aspect, the invention relates to a combination that includes a pelvic implant and an adjusting tool, the combination being useful to treat a pelvic condition. The implant includes a tissue support portion, an extension portion, and an adjusting mechanism at a distal end of the extension portion. The adjusting tool includes a surface capable of engaging the adjusting mechanism while the adjusting mechanism is implanted subcutaneously in a patient.

In another aspect the invention relates to a method of treating a pelvic condition. The method includes: providing a pelvic implant useful to treat a pelvic condition, the implant including a tissue support portion, an extension portion, and an adjusting mechanism at a distal end of the extension portion, the adjusting mechanism capable of being actuated to adjust a length of the extension portion; providing an adjusting tool capable of engaging the adjusting mechanism while the adjusting mechanism is implanted subcutaneously in a patient; placing the implant in a patient to support tissue with the adjusting mechanism located subcutaneously; and post-operatively engaging the adjusting tool with the adjusting mechanism to actuate the adjusting mechanism and adjust a length of the extension portion.

Figure 1:
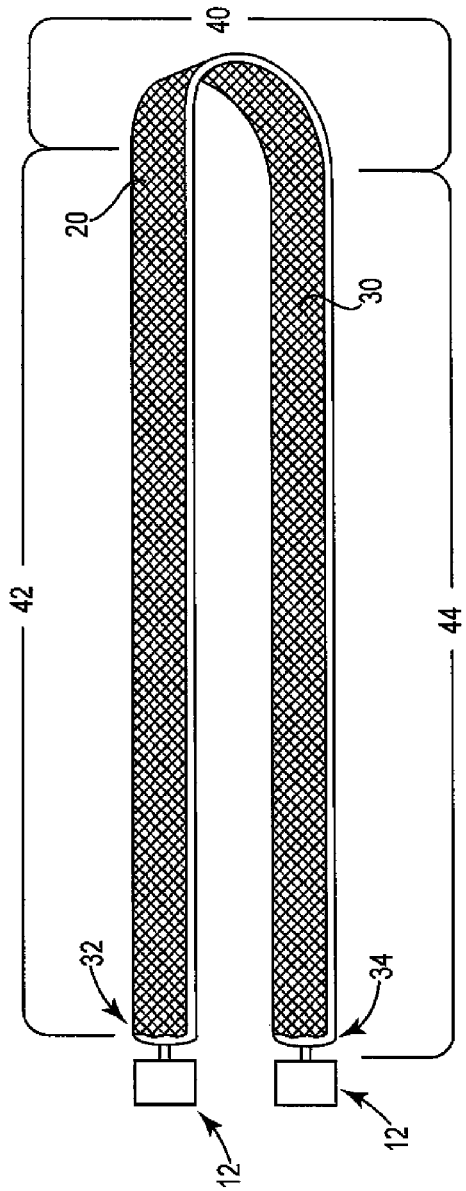
FIGS. 1 and 2 show an embodiment of an implant as described.
Figure 2:
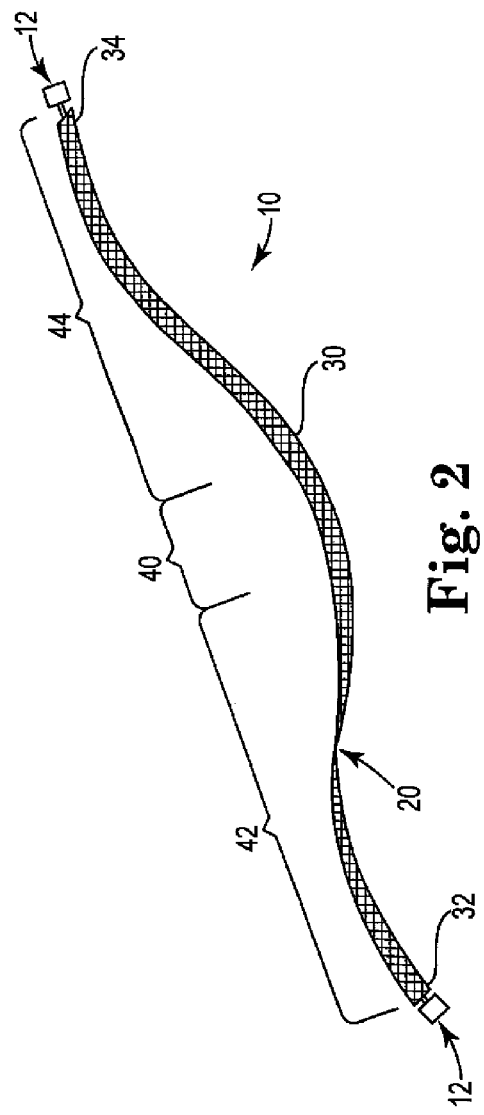

All drawings are not to scale.

DETAILED DESCRIPTION

Pelvic floor disorders include urinary and fecal incontinence, prolapse, cystocele, rectocele, enterocele, uterine and vaginal vault prolapse, levator defects, and others, in male and female patients. These disorders typically result from weakness or damage to normal pelvic support systems. Common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures for treating urinary incontinence include surgical methods that place a supportive implant such as a sling to stabilize or support the bladder neck or urethra. Various supportive implants and sling procedures are known. Slings and methods can differ based on the type of sling material and anchoring methods used, and placement and technique for placing and supporting the sling, including tissue to be supported. According to some past procedures, a sling is placed under the bladder neck and secured via suspension sutures to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686, 6,042,534 and 6,110,101.

In accordance with other methods and devices of the invention, implants as described can be useful for treating vaginal prolapse, such as vaginal vault prolapse. Accordingly, an implant having an adjustable length, e.g., comprising an adjusting mechanism as described herein, can be pre-attached to a vagina at one end, and at or near a sacrum (i.e., a component of sacral anatomy) at a second end. The end located at or near the sacrum can include an adjusting mechanism as described herein. A physician can adjust the tension and length of the implant between a vagina and sacrum, when securing the vagina to the sacrum through a single vaginal incision. Post-operatively, e.g., within 1, 2, or 3 days, to 1, 2, or 3 weeks after the surgical procedure, a physician can again adjust the tension by actuating the adjusting mechanism.

As used herein, the terms "anchor," "tissue fastener," and "self-fixating tip," refer interchangeably and non-specifically to any structure that can connect an implant to supportive tissue of a pelvic region. The supportive tissue may preferably be a soft tissue such as a muscle, fascia, ligament, tendon, or the like. The anchor may be any known or future-developed structure useful to connect an implant to such tissue, including but not limited to a clamp, a suture, a soft tissue anchor such as a self-fixating tip, and the like.

An implant can include a tissue support portion (or "support portion" or "center support portion") that can be used to support tissue as desired, e.g., a urethra (including a bladder neck), bladder, vagina, levator, rectum, sphincter, or other pelvic tissue. Supporting a "urethra" refers to supporting tissue that includes the urethra (which can refer to the bladder neck), and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally, for treating incontinence, an implant can include two opposing extension portions. Extension portions are elongate pieces of material (e.g., mesh, molded implant material, suture, or biologic material) that extend from the tissue support portion and either are or can be connected to the tissue support portion, and are useful to attach to anatomical features or "supportive tissue" in the pelvic region (e.g., using an anchor such as a self-fixating tip or another form of tissue fastener, or an adjusting mechanism as described here) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's copending United States Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference). Also see U.S. Patent Publication number US 2011/0034759 and WO 2010/093421, PCT/US2010/057879, filed Nov. 23, 2010, and PCT/US2010/059739, filed Dec. 9, 2010, the entireties of which are incorporated hereby by reference.

In exemplary uses, each extension portion can extend from the location of attachment with the tissue support portion of the implant, through pelvic tissue, and to a location of supportive tissue within the pelvic region, preferably near the patient's skin. The supportive tissue can be at an end of a tissue path used to perform a desired implant procedure, such as at a location near an external incision in the skin used to perform the procedure, e.g., at a location at or near an end of an extension portion placed according to a retropubic procedure or a transobturator procedure for placing a sling for treating urinary or fecal incontinence.

An implant may include portions, pieces, or sections that are synthetic or of biologic material (e.g., porcine, cadaveric, etc.). Extension portions may be, e.g., a synthetic mesh such as a polypropylene mesh, a suture, a biodegradable suture, a molded implant material, or the like. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and AdVance™ for treating urinary incontinence.

An example of a pelvic implant that may be useful according to this description is the type that includes supportive portions including or consisting of a tissue support portion and two or four extension portions extending from the tissue support portion. An implant that has exactly two or four extension portions can be of the type useful for treating urinary incontinence, fecal incontinence, or a combination of vaginal prolapse and urinary or fecal incontinence. The term "supportive portions" refers to portions of an implant that function to support tissue after the implant has been implanted and specifically includes extension portions and tissue support portions, and does not include optional or appurtenant features of an implant such as a sheath, tensioning suture, tissue fastener, or self-fixating tip or other type of connector for attaching the implant to an insertion tool.

Dimensions of a tissue support portion can be any dimensions useful to support a specific tissue, e.g., urethral or vaginal tissue, for treating a pelvic condition such as incontinence, prolapse, or another pelvic condition. A tissue support portion for use in treating incontinence can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters.

An implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending United States Patent Publication Number US 2006/0287571 and U.S. Pat. No. 7,422,557, the entireties of these applications being incorporated herein by reference.

Dimensions of extension portions can allow the extension portion to reach between a tissue support portion placed to support a pelvic tissue such as tissue of a urethra, vagina, anal sphincter, levator, etc., (at an end of the extension portion connected to the tissue support portion) and a location at which the distal end of the extension portion attaches to an adjusting mechanism that can be actuated to increase or decrease the length of the extension portion. The adjusting mechanism is preferably located at tissue of the patient's pelvic region, preferably at a subcutaneous location adjacent to the patient's skin. As used herein, "subcutaneous" refers to a location that is below the skin of the patient, but near an external surface of the skin, such as within two inches, one inch, or a half inch of the outer surface of the patient's skin. Exemplary lengths of an extension portion for use in treating incontinence, for example, measured between a connection or boundary between the extension portion and the tissue support portion, and a distal end of the extension portion that connects to the adjusting mechanism, can be, e.g., from 0.5 to 3 inches, preferably from 1.0 to 2.5 inches, the length being adjustable as described herein. These or other lengths will be useful for implants designed to treat other conditions. For example, lengths of a sling for treating anal incontinence may be longer.

Implants as described can alternately include a dilator, connector, tissue fastener, or an adjusting mechanism as described, at a distal end or a distal portion of an extension portion, which is the end or portion not attached to a tissue support portion. (The term "distal" as used in this context generally refers to location at an end of an extension portion away from a tissue support portion.) A dilator, connector, or tissue fastener can be any of various types, including: a dilator or connector that facilitates passage of the extension portion through a tissue path, e.g., by connecting to an end of an insertion tool; a self-fixating tip that facilitates passage of the extension portion through a tissue path (using an insertion tool) and that can be secured to supportive tissue. Useful examples of dilators, connectors, and tissue fasteners are well known. Generally preferred tissue fasteners include those referred to as "self-fixating" tips, which can be inserted into soft tissue and frictionally retained. Others include other forms of soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007; U.S. patent application Ser. No. 12/223,846, filed Aug. 8, 2008, entitled SURGICAL ARTICLES AND METHODS FOR TREATING PELVIC CONDITIONS; U.S. patent application Ser. No. 12/669,099, filed Jan. 14, 2010, entitled PELVIC FLOOR TREATMENTS AND RELATED TOOLS AND IMPLANTS; and WO 2009/075800, the entireties of which are incorporated herein by reference.)

According to various systems as described, one or more instrument, insertion tool, adjustment tool, or the like, may be used with an implant or method as described. Examples of useful tools include those that generally include one or more (stationary or moveable) thin elongate, relatively rigid shaft or needle that extends from a handle. The handle is located at a proximal end of the tool and attaches to one end (a proximal end) of the shaft. An exemplary shaft of an insertion tool can be useful to form or pass through a tissue path between a location of placement of a tissue support portion, and a location of placement of an end of an extension portion, e.g., a location of placement of an adjusting mechanism. According to some embodiments, a distal end of one or more shaft can be adapted to engage a distal end of an extension portion or a component thereof, such as a tissue fastener (e.g., a self-fixating tip), a dilator, or an adjusting mechanism, in a manner that allows the insertion tool to either push or pull the tissue fastener (e.g., a self-fixating tip), dilator, or adjusting mechanism, through a tissue path used for placement of an extension portion of an implant.

Examples of insertion tools that may be useful for forming a tissue path or placing an extension portion, optionally with modification, for treating vaginal prolapse, are described, e.g., in U.S. patent application Ser. Nos. 10/834,943, 10/306, 179; 11/347,553; 11/398,368; 10/840,646; PCT application number 2006/028828; PCT application number 2006/0260618; WO 2010/093421, and US Patent Publication No. 2010-0256442 the entireties of these documents being incorporated herein by reference.

One general form of implant useful for treatment of urinary or fecal incontinence as described herein is a suburethral or retropubic sling, e.g., as marketed by American Medical Systems under various trade names including MONARC™, SPARC™, INVANCE, ADVANCE™. Devices and methods as described can be suitable for these and similar slings in the treatment of male and female urinary and fecal incontinence and to effect pelvic floor, perineal floor, and pelvic prolapse repairs that involve a variety of surgical approaches. For example, female pelvic floor repair slings may be implanted by techniques that involve transvaginal, transobturator, suprapubic, pre-pubic, or transperineal exposures or pathways. Male urinary incontinence slings may be implanted by techniques that involve transobturator, suprapubic, or transperineal pathways. Embodiments of the described devices and methods may be useful in treating fecal incontinence, by use of a transvaginal, transobturator, suprapubic or perineal floor pathway. In fecal incontinence applications, the disclosed embodiments can be used to correct the anorectal angle in the rectum to re-establish continence in patients. The above methods can, but are not necessarily limited to, use of helical needles of the type described in U.S. Pat. No. 6,911, 003 or C-shaped needles or elongate needles of the type used to perform suprapubic procedures.

Referring to FIG. 1, an exemplary embodiment of an elongated sling assembly 10 is depicted in which the embodiments of the present invention may be advantageously implemented. Sling assembly 10 contains sling 20 that may be implanted in any of the above-described manners and pathways through which at least end portions of elongated sling assembly 10 are drawn to dispose central support portion 40 in operative relation to a urethra, bladder neck, anal sphincter, or other supported tissue. Sling assembly 10 comprises sling 20 coupled to two adjusting mechanisms 12, each located at an end of sling 20. The depicted exemplary sling assembly 10 thus extends between two opposing adjusting mechanisms 12 that can be placed at locations near an outer surface of a patient's skin, while sling 20 is placed to support a pelvic tissue.

Sling 20 is designed to be implanted and then left in place chronically, and includes an elongated, rectangular (in this depicted embodiment) braided or preferably knitted, mesh strip or simply mesh 30. Sling 20 and mesh 30 are subdivided into a central support portion 40 adapted to be placed below tissue to be supported, such as a urethra. In a female patient, support portion 40 can be placed between the urethra or bladder neck and the vaginal wall. End portions 42 and 44 extend from the central support portion 40 to the mesh ends 32 and 34. In FIGS. 1-5, the mesh 30 extends between mesh ends 32 and 34 and may be continuous throughout the length of sling 20 between mesh ends 32 and 34. However, it will be understood that the central portion 40 of sling 20 may be formed of other materials such that the central portion 40 is physically attached to the end portions 42 and 44. In certain embodiments, central portion 40 may be formed of any tissue-compatible synthetic material or any natural biocompatible material, including, but not limited to, treated autologous, allograft, or xenograft tissues, porcine dermis, a tissue engineered matrix, or a combination thereof. Mesh 30 may be dimensioned and shaped for treatment of male and female urinary and fecal incontinence and to effect pelvic floor, perineal floor, and pelvic prolapse repairs using a variety of surgical approaches. For example, sling 20 may comprise more than two end portions 42 and 44 coupled to any of a connector, dilator, or tissue fastener, and extending at a variety of angles from a particularly shaped center portion 40.

In use, sling ends 32, 34 and adjusting mechanisms 12 can be placed in a desired tissue path, optionally by connecting (separately) either or both adjusting mechanism to an implantation tool and drawing each adjusting mechanism through a tissue pathway in which an extension portion will be located. Central support portion 40 is adapted to draw against tissue to support urethra, bladder neck, anal sphincter, or other tissue of a pelvic region after end portions 42 and 44 are drawn through tissue pathways between the central support portion and external incisions adjacent to opposing locations of subcutaneously placed adjusting mechanisms 12. As an example, using an insertion tool, adjusting mechanisms 12 may be drawn from a location near a medial incision (e.g., vaginal or perineal), away from the medial incision, toward two opposed external lateral incisions in the patient's skin. The external lateral incisions may be at locations of an abdomen or a groin, e.g., to allow for retropubic or transobturator tissue paths, respectively. The adjusting mechanism can be placed and retained at tissue at a subcutaneous location, below the surface of the skin at the location of the external lateral incision. The lateral incisions are closed and sling 20 remains in place. Post-operative adjustment of the tension or length of sling 20 can be made to provide ongoing urethral or anal resistance to leakage.

Figure 3:
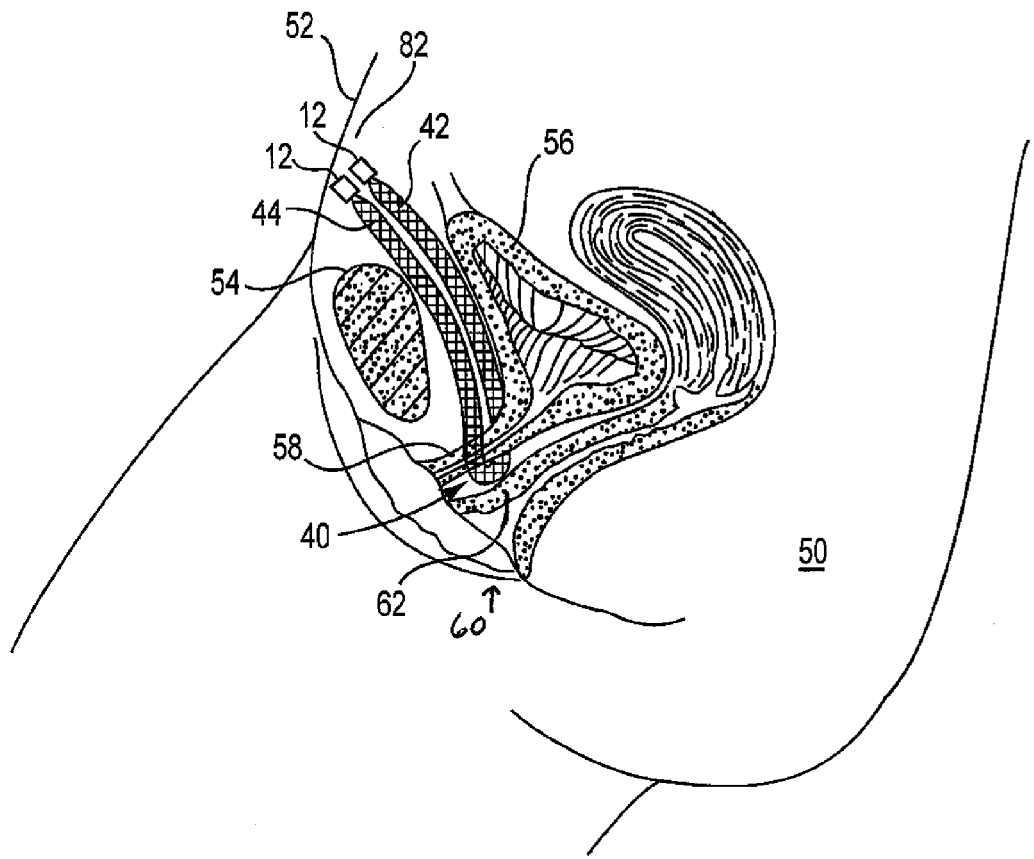
FIGS. 3, 4, and 5 show embodiments of implants and selected anatomy.

FIG. 3 illustrates an example of anatomy relevant to an implantation procedure that results in sling 20 extending through tissue pathways created in a female (for example) patient 50 extending around urethra 58. In preceding steps, tissue pathways were formed by passing needles through a vaginal skin incision 62 just adjacent to vagina 60, through soft tissue between urethra 58 and vagina 60, and along each side of urethra 58 through layers of fat, muscle, and fascia, and between pubic bone 54 and bladder 56 to first and second skin incisions through skin 52. Any of the known tissue pathways may be formed in this generally described manner. In alternate embodiments a sling can be implanted via a single incision (vaginal incision 62, or a perineal incision, e.g., in a male patient) with opposing extension portions being placed in opposing tissue paths that extend more laterally, through opposing obturator foramen, and to external incisions at a location of an inner groin. In either embodiment, adjusting mechanisms 12 become located in the patient subcutaneously, below and near the outer surface of the skin. Extension portions 42 and 44 were brought into position in the tissue paths by use of one or more insertion needle that was attached to an extension portion or an adjusting mechanism 12, then drawn or pushed through the tissue path.

Figure 4:
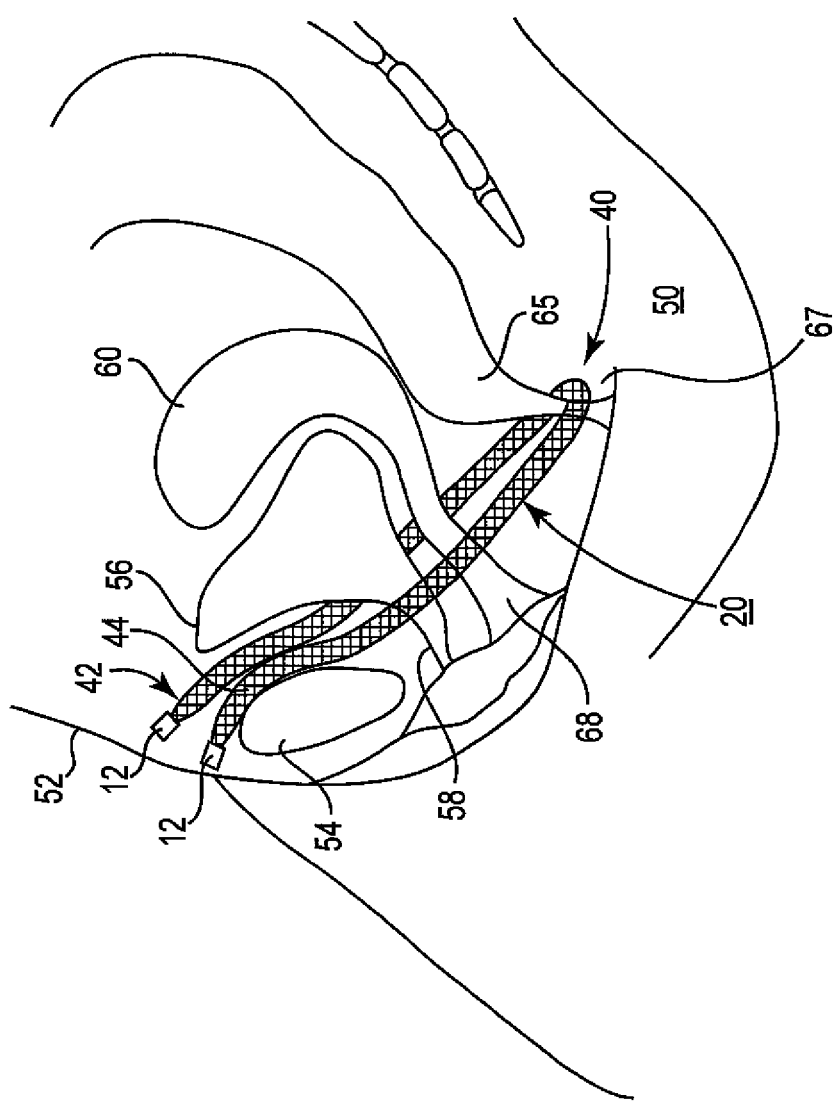

Referring to FIG. 4, a schematic illustration of an incontinence sling implanted in a female (for example) patient's body for treating fecal incontinence is depicted. In this illustration, the sling central portion 40 extends underneath the anus or anal sphincter 67 or inferior portion of the rectum 65 (hereafter collectively referred to as the anus 67 for convenience) to correct the anorectal angle in the patient. Adjusting mechanisms 12 are located subcutaneously, below and near the outer surface of the skin. Various surgical approaches can be used to implant sling 20 to correct fecal incontinence including suprapubic, transobturator, retropubic, prepubic, transperineal and transvaginal (including a single incision approach transvaginally or transperineally).

Figure 5:
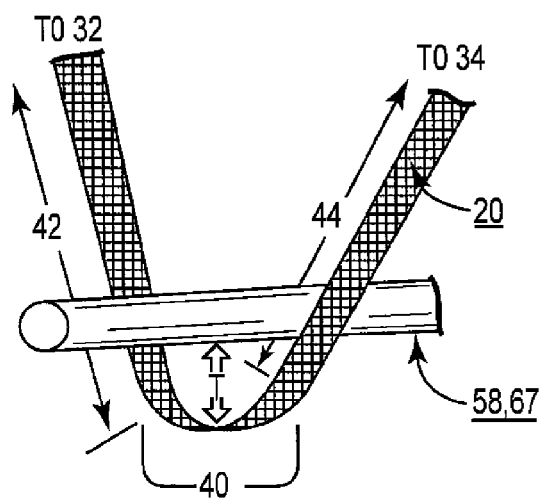

At this point, the tension T that sling 20 applies against the urethra 58 or anus 67 is adjusted as schematically illustrated in FIG. 5. Because the procedure may be performed using a local anesthesia, the patient 50 is able to provide feedback to the surgeon during adjustment of sling tension. In the procedure illustrated in FIG. 5, typically, bladder 56 is filled with saline using a catheter, and the patient is requested to cough. The surgeon is able to determine whether leakage occurs and may adjust the tension on the sling 20 to increase tension of the center support portion 40 against the urethra 58. Adjusting mechanisms 12 are placed and secured as desired at subcutaneous locations, and the external (e.g., abdominal) incisions and the central (e.g., vaginal, or groin or labia fold incisions for a transobturator approach) are closed.

Figure 6A:
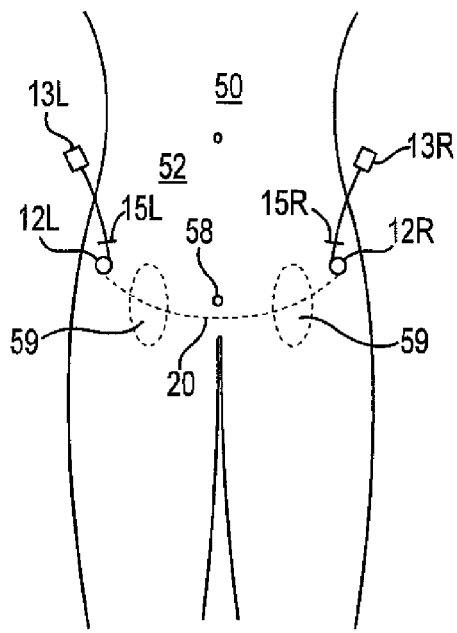
FIGS. 6A, 6B, 7A, and 7B show embodiments devices and of anatomy relevant to described methods.
Figure 6B:
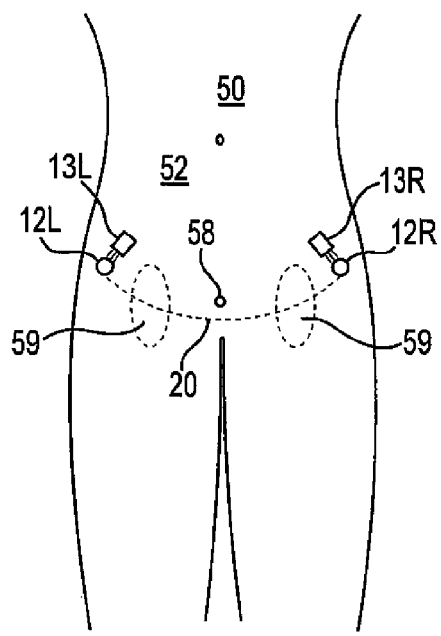

In various embodiments of described devices and methods, a length or tension of sling 20 can be adjusted in a post-operative step to adjust tension applied to a urethra 58 or anus 67 to enhance efficacy and patient comfort. Referring to FIGS. 6A and 6B, sling 20 is implanted to provide treatment for, e.g., incontinence. Adjusting mechanisms 12 are at opposing ends of sling 12, and upon implantation of are placed at opposing sides of the patient, below the skin of the patient.

FIGS. 6A and 6B show implant 20 inserted to support urethra (or other tissue) 58 with extension portions extending laterally through opposing transobturator tissue paths, through opposing obturator foramen 59, each tissue path ending at a lateral external incision. As shown at FIG. 6A, in a post-operative step, left adjusting mechanism 12L is being adjusted using adjustment tool 13L, which has been passed through external incision 15L. Optionally and preferably, a second adjustment tool, 13R can be used in a coordinated post-operative adjusting step to actuate right adjusting mechanism 12R, through external incision 15R. Coordinated adjustment of adjusting mechanisms 12L and 12R—meaning that the tension or length of both of the two extension portions of sling 20 are adjusted at the same time—can advantageously allow a surgeon or other user to adjust the placement, length, or tension of implant 20 in a manner that does not cause urethra (or other tissue) to become located at a non-anatomical position relative to a midline of the patient. Stated differently, left and right adjusting mechanisms 12L and 12R can be adjusted together to prevent the urethra or other supported tissue from being moved in a left or a right direction within the patient, which will maintain a correct anatomical position of the urethra or other supported tissue, e.g., at a midline of the patient.

In a similar but not identical fashion, FIG. 6B illustrates an implant as at FIG. 6A, but that is adjusted by use of external adjustment tools 13L and 13R that do not pass through an external incision in the skin of the patient, but that can communicate with adjusting mechanisms 12L and 12R transcutaneously, through the patient's intact skin, e.g. by a transcutaneous frictional engagement, a magnetic engagement, or by any other useful mechanism by which an external adjustment tool (13L, 13R) can communicate with an adjusting mechanism (12L, 12R) through a patient's intact skin.

Figure 7A:
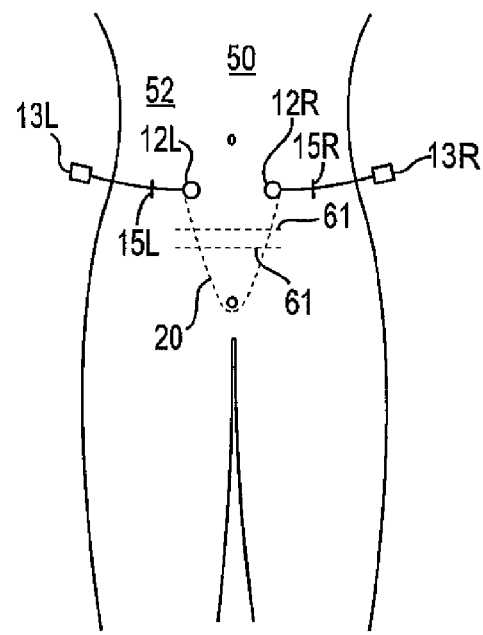
Figure 7B:
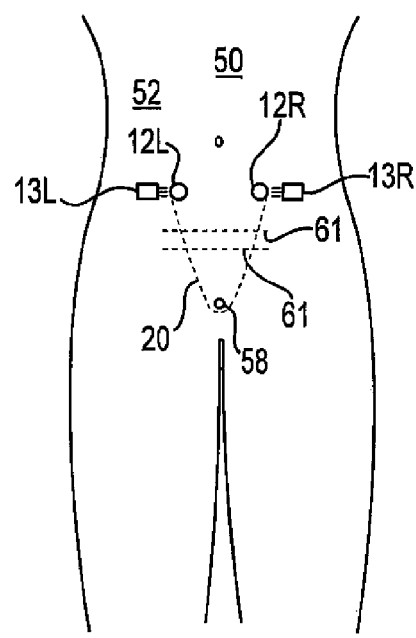

FIGS. 7A and 7B show implant 20 inserted to support urethra (or other tissue) 58 with extension portions extending through opposing retropubic tissue paths, behind pubic symphysis 61, each tissue path ending at an abdominal external incision. As shown at FIG. 7A, in a post-operative step, left adjusting mechanism 12L is being adjusted using adjustment tool 13L, which has been passed through incision 15L. Optionally and preferably, a second adjustment tool, 13R can be used in coordinated post-operative adjusting step to actuate right adjusting mechanism 12R through external incision 15R. Coordinated adjustment of adjusting mechanisms 12L and 12R—meaning that the tension or length of both of the two extension portions of sling 20 are adjusted at the same time—can advantageously allow a surgeon or other user to adjust the placement, length, or tension of implant 20 in a manner that does not cause urethra (or other tissue) to become located at a non-anatomical position relative to a midline of the patient.

In a similar but not identical fashion, FIG. 7B illustrates an implant as at FIG. 7A but that is adjusted by use of external adjustment tools 13L and 13R that do not pass through an external incision in the skin of the patient, but that can communicate with adjusting mechanisms 12L and 12R transcutaneously, through the patient's intact skin, e.g. by a transcutaneous frictional engagement, a magnetic engagement, or by any other useful mechanism by which an external adjustment tool (13L, 13R) can communicate with an adjusting mechanism (12L, 12R) through a patient's intact skin.

Referring to FIGS. 8A, 8B, 8C, 8D, 8E, 8F, and 8G illustrated are examples of a non-invasive adjusting mechanisms 12 and adjustment tools 13 that can be used to transcutaneously increase or decrease tension in an implant, i.e., through intact tissue (skin) of a patient, without the need for a surgical incision to access an associated internally-placed adjusting mechanism. Adjusting mechanism 12 can be actuated without invasive means by using a external adjustment tool 13.

Referring to FIGS. 8A, 8B, 8C, and 8D, adjusting mechanism 12 can be actuated to provide tension on a component of an implant (e.g., a suture or mesh of an extension portion) without performing surgery or creating an external incision. External adjustment tool 13 can be used to communicate with or engage internal adjusting mechanism 12, through skin 52. In use, an implant (e.g., incontinence sling) is placed to support tissue. The implant includes an extension portion (42 or 44) that is connected to adjusting mechanism 12. The connection may be any useful connection that allows adjusting mechanism 12 to reduce a length of the extension portion (e.g., as measured to be a length between a central support portion and adjusting mechanism 12). As illustrated, a distal end of extension portion 42 or 44 may be in the form of a mesh, suture, line, or other elongate material that is sized to allow the distal end of the extension portion to become wound upon spool 90 upon actuation of adjusting mechanism 12. External adjustment tool 13 can include a mechanical, magnetic, or electromagnetic coupling that communicates with internal adjusting mechanism 12, and external adjustment tool 13 can be used to activate the internal adjusting mechanism 12 to add or reduce tension on the implant.

Figure 8A:
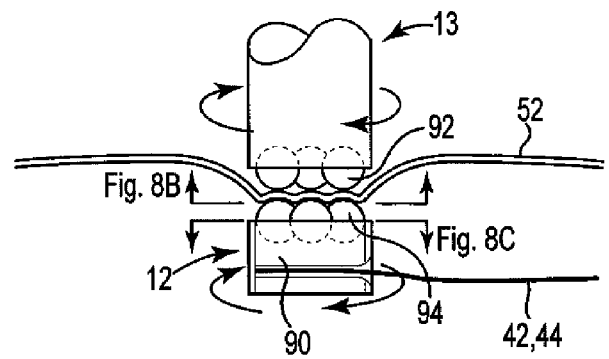
FIGS. 8A, 8B, 8C, 8D, 8F, 8E, and 8G show embodiments of devices as described.
Figure 8B:
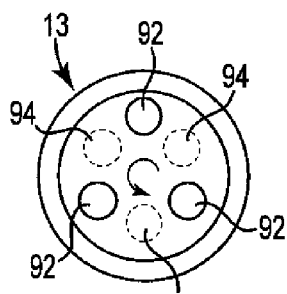
Figure 8C:
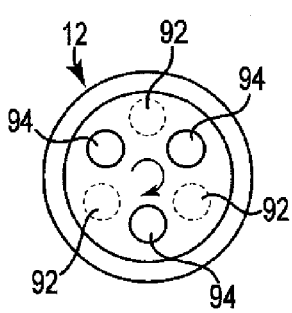
Figure 8D:
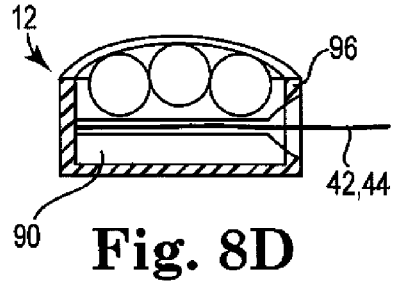

FIGS. 8A, 8B, and 8C illustrate one exemplary mechanical engagement mechanism between an internal adjusting mechanism 12 and an external adjustment tool 13. Internal adjusting mechanism 12 can be activated to increase or decrease tension on a component of an implant, such as a mesh or suture 42 or 44, which is a distal component of an extension portion. The increase or decrease in tension can be accomplished by any mechanical mode, such as by winding spool 90. The engagement between internal adjusting mechanism 12 and external tool 13 can occur through the intact tissue (e.g., epidermis, skin) of the patient. As shown at FIGS. 8A, 8B, and 8C, a useful engagement can be a mechanical engagement that allows transdermal mechanical engagement of internal adjusting mechanism 12 with external tool 13.

The mechanical engagement can include relatively smooth and rounded surfaces such as hemispheres or other curved surfaces that can engage through the skin with sufficient mechanical force to allow the external adjustment tool 13 to mechanically manipulate internal adjusting mechanism 12. Desirably, the mechanical engagement does not include any sharp surfaces that would damage the patient's internal or external tissue. The mechanical engagement can be one that can allow an operative connection between a surface of internal adjusting mechanism 12 and a surface of external adjustment tool 13, with sufficient intimacy and strength that when the engagement is made through the patient's intact skin, movement of the external adjustment tool causes desired, predictable, dependable, and effective movement of the internal adjusting mechanism in a desired direction (e.g., turning clockwise or counterclockwise) to effect a dependable turning motion of spool 90 within casing 96 to either wind or unwind mesh or suture 42 or 44 through the patient's tissue.

As illustrated at FIGS. 8A through 8D, opposing mechanical surfaces of internal adjusting mechanism 12 and external adjustment tool 13 can exhibit general size and shape features to allow the surfaces to move over tissue surfaces without damaging the tissue or causing undue patient discomfort. Useful shapes may be curves without jagged or sharp edges. As illustrated at FIG. 8B, showing an end surface of external adjustment tool 13, an effective surface may include moveable or stationary spheres or hemispheres 92 or similarly curved surface structures that are complementary to opposing surfaces adjusting mechanism 12. Moveable or stationary spheres or hemispheres 92 can be fixed rounded hemispheres, or rolling spheres. FIG. 8C shows such an opposing and complementary end surface of adjusting mechanism 12, having three moveable or stationary spheres or hemispheres 94, which may be fixed rounded hemispheres or rolling spheres. In use, the end face of external adjustment tool 13 can be placed against skin 52, with sufficient pressure for spheres or hemispheres 92 to transcutaneously engage spheres or hemispheres 94 of adjusting mechanism 12. With the transcutaneous engagement intact, external adjustment tool 13 can be rotated about a longitudinal axis (see arrows). Rotational movement of spheres or hemispheres 92, engaged with spheres or hemispheres 94, causes rotational movement of spool 90 of internal adjusting mechanism 12, which will in turn cause winding or unwinding of a length of mesh or suture 42 or 44.

Figure 8E:
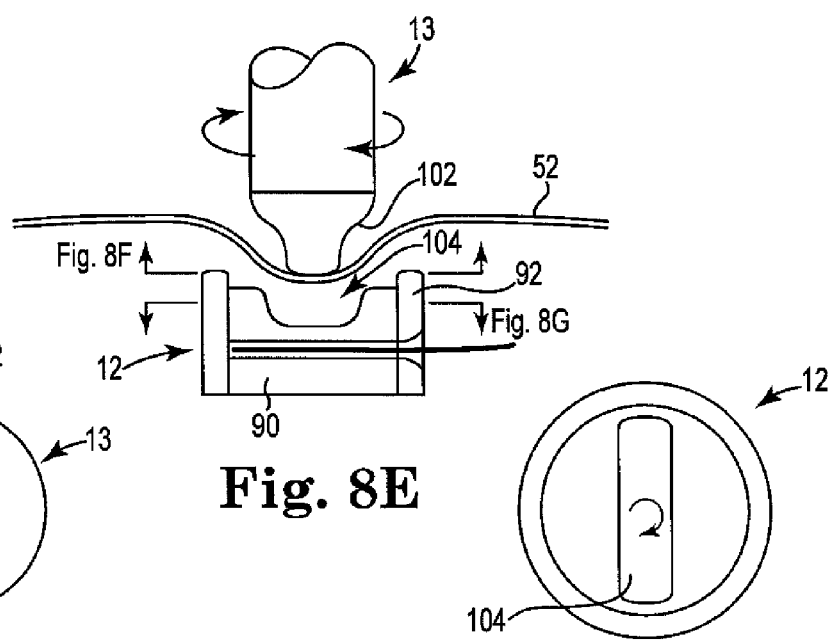
Figure 8F:
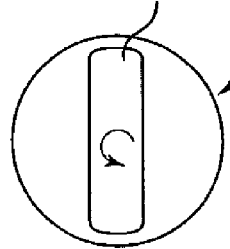
Figure 8G:
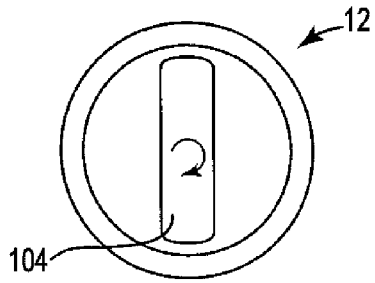

FIGS. 8E, 8F, and 8G show an alternate embodiment of adjusting mechanism 12 and adjustment tool 13 wherein the non-mechanical engagement between internal adjusting mechanism 12 and the external adjustment tool 13 is in the form of a rounded blade and slot, which allow for a transcutaneous mechanical engagement. Internal adjusting mechanism 12 includes slot 104, which can be transcutaneously engaged by blade 102 of external adjustment tool 13. These include curved edges that allow the surfaces to move over tissue surfaces without damaging the tissue or causing undue patient discomfort. FIG. 8F illustrates an end surfaces of blade 102, and FIG. 8G illustrates an end surface of complementary slot 104. In use, blade 102 of external adjustment tool 13 can be placed against skin 52 with sufficient pressure for blade 102 to transcutaneously engage slot 104 of adjusting mechanism 12. With the transcutaneous engagement intact, blade 102 can be rotated about a longitudinal axis (see arrows). Rotational movement of blade 102, engaged transcutaneously with slot 104, causes rotational movement of spool 90 of internal adjusting mechanism 12, which will in turn cause winding or unwinding of a length of mesh or suture 42 or 44.

Optionally, (for any such transcutaneous engagement) additional engagement force can be provided by opposing magnets present on external adjustment tool 13 and adjusting mechanism 12. Receiving spool 90 can include a magnet that rotates when the external magnet is rotated. The non-mechanical, magnetic engagement could be used in combination with a mechanical engagement.

FIGS. 9A through 9D show another embodiment of an implant that includes an adjusting mechanism useful to adjust a length or tension of an implant (e.g., a length of an extension portion) and related method. FIG. 4A illustrates implant 120 (e.g., urethral sling or other form of implant) having a central support portion and two elongate end portions. Tissue fastener (e.g., self-fixating tip) 122 is located at a distal end of one end portion. Adjusting mechanism 124 is located at a distal end of the other end portion. In alternate embodiments, an adjusting mechanism 124 may be located at both ends of the implant. Filament 126 (e.g., suture) extends between mesh 128 of implant 120 and adjusting mechanism 124. Adjusting mechanism 124 can be actuated in a transcutaneous manner, by an adjustment tool that communicates with actuating mechanism 124 through a patient's intact skin. Alternately, adjusting mechanism 124 can be actuated in by an actuating tool that passes through an incision in the patient's skin to contact and connect with actuating mechanism 124 during actuation.

Adjusting mechanism 124 can be placed at a subcutaneous location in a patient, with implant 120 supporting tissue as described. Adjusting mechanism 124 is capable of winding or otherwise reducing the length of filament 126. Tissue fastener 112 is attached directly to mesh 128. In use, tissue fastener 122 can be installed at supportive tissue at one side of a patient. Adjusting mechanism 124 can be installed at the opposite side of the patient. Mesh 128 is positioned to support tissue 58 (e.g., a urethra, bladder, vaginal tissue, or another tissue) (see FIG. 9A). Adjusting mechanism 124 can be activated to reduce the length of filament 126 between adjusting mechanism 124 and mesh 128, causing a reduction in the total length of implant 120 and causing implant 120 to more closely support tissue 58 (see FIG. 9B). Adjusting mechanism 124 can be any mechanism that can collect a length of filament 126, such as by winding on a spool or by a spring mechanism. The length of filament 126 can be reduced by use of adjusting mechanism 124, preferably so that substantially the entire length of filament is collected at the winding mechanism and the implant extending between tissue fastener 112 and adjusting mechanism 124 is substantially entirely mesh. In alternate embodiments, an adjusting mechanism 124 may be located at both ends of the implant, and the adjusting mechanisms may be used in a coordinated manner to prevent tissue 58 from being moved laterally during adjustment.

Figure 9A:
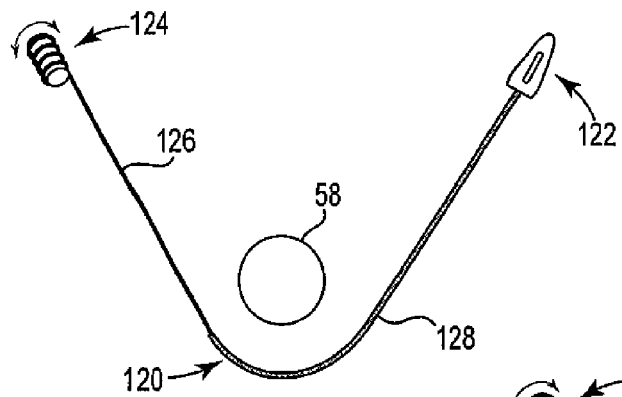
FIGS. 9A, 9B, 9C, and 9D show embodiments devices and of selected anatomy relevant to described methods.
Figure 9B:
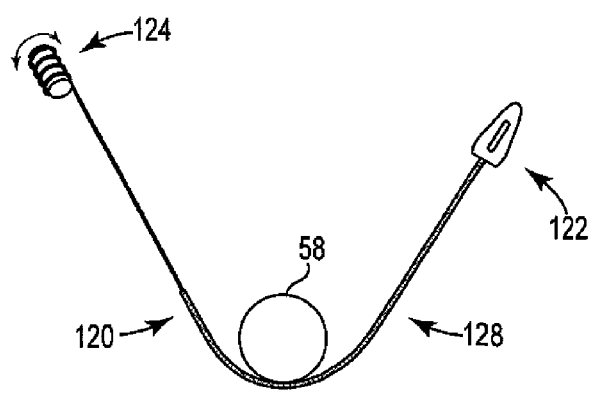
Figure 9C:
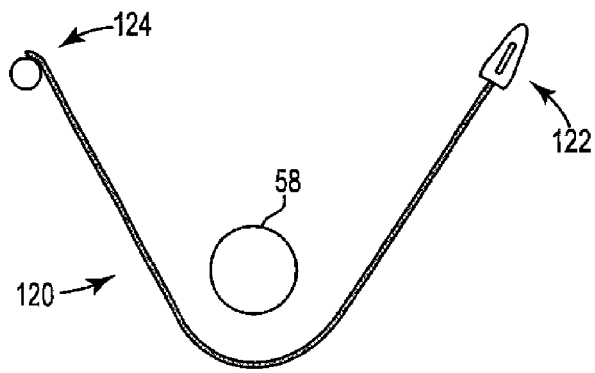
Figure 9D:
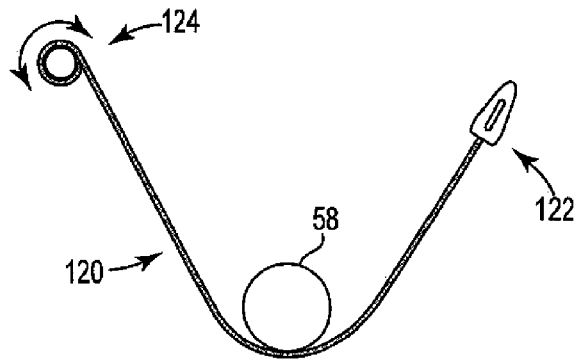

FIGS. 9C and 9D show an alternate embodiment of implant 120. In this embodiment, implant 120 does not include a filament 126. Instead, implant 120 is a mesh strip extending entirely between adjusting mechanism 124 and tissue fastener 122. Adjusting mechanism 124 winds or otherwise collects the mesh to adjust the length or tension of implant 120. In alternate embodiments, an adjusting mechanism 124 may be located at both ends of the implant, and the adjusting mechanisms may be used in a coordinated manner to prevent tissue 58 from being moved laterally during adjustment.

Figure 10A:
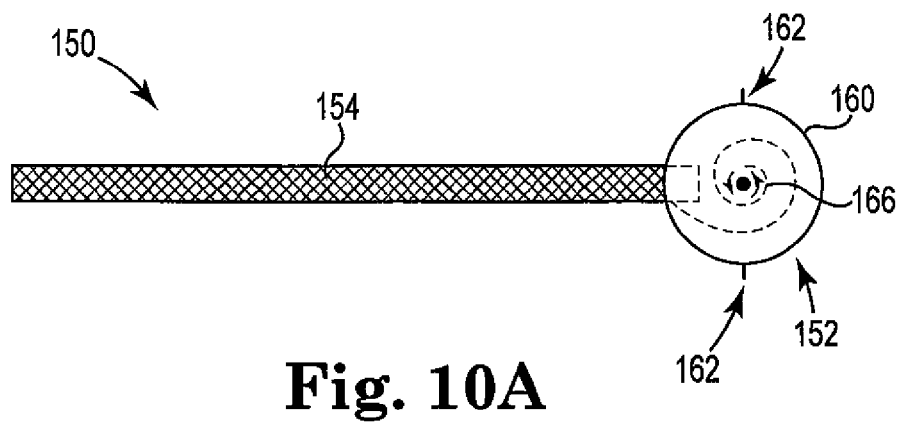
FIGS. 10A and 10B show embodiments of devices as described.

Referring to FIG. 10A, an exemplary implant 150 is illustrated. Implant 150 includes mesh 154 attached at one end to adjusting mechanism 152. Adjusting mechanism 152 allows for non-invasive adjustment (e.g., increasing or decreasing) of tension of the implant (e.g., urethral sling, or other form of implant) after implantation, without the need for additional surgery an additional incision to access the adjusting mechanism 152. Increasing or decreasing the tension on an implant or portion of an implant can be accomplished by the use of adjusting mechanism 152, to which the mesh of an implant, such as a sling, can be attached. As is illustrated in the exemplary embodiment of FIG. 10A, an elongated piece of mesh 154 is attached directly or indirectly to motor 166 within housing 160 at an end of implant 150. Motor housing 160 includes motor 166, which is illustrated as being generally in the center of motor housing 160, although it is understood that it is not necessary that the motor be in the center of the housing. Motor housing 160 is provided with a size that is sufficient to contain or hold as much of the length of mesh 154 as may be expected to be spooled within the housing, as is described below. Motor 166 can be activated by any useful mechanism, such as by use of an external adjustment tool as described herein, or another mechanical, electronic, electromagnetic, or other communicative device To shorten the length of implant 150, motor 166 is activated to cause rotation of a component of the adjusting mechanism (e.g., a central core) to wind up or "spool" mesh 154 within housing 160 until a desired tightness of implant 150 within the patient is achieved. Such a system can additionally or alternately allow for lengthening of implant 150 to provide more "slack" or to loosen implant 150 within a patient. To accomplish this, motor 160 can be activated to unwind mesh 154, such as by causing rotation in an opposite direction from the direction in which the adjusting mechanism rotates to shortening mesh 154. Motor 166 can provide for rotation in only a single direction (e.g., counterclockwise rotation), or can alternately provide for movement of the motor housing in two directions (e.g., clockwise and counterclockwise rotation). Movement of the motor housing in two opposing directions will allow for both tightening and loosening of the implant, such as if the original implantation procedure provided for a mesh that is too loose or tight or if the procedure of tightening the mesh within the motor housing caused excessive tension in the mesh material.

Adjusting mechanism 152 can be provided with exterior holding or anchoring structure 162, such as suture hoops, stays, barbs, anchors, or other structure or devices on exterior surfaces that can be used to secure adjusting mechanism 152 to tissue or to strengthen a grip between adjusting mechanism 152 and adjacent tissue, to provide compensating torque or force on housing 160 during adjustment. When, for example, suture hoops are provided, sutures or devices can be attached to the suture hoops to provide motor housing rotation control. Other devices or systems can be used in addition to or as a replacement for the suture hoops to provide compensating torque or force. To measure or monitor the force on material 156, adjusting mechanism 152 can further be provided with torque or force transducers to measure a tensioning force. Such transducers can be used on the implant itself or the motor to provide the surgeon with feedback regarding the relative degree of tension or positioning of the implant within the patient.

Figure 10B:
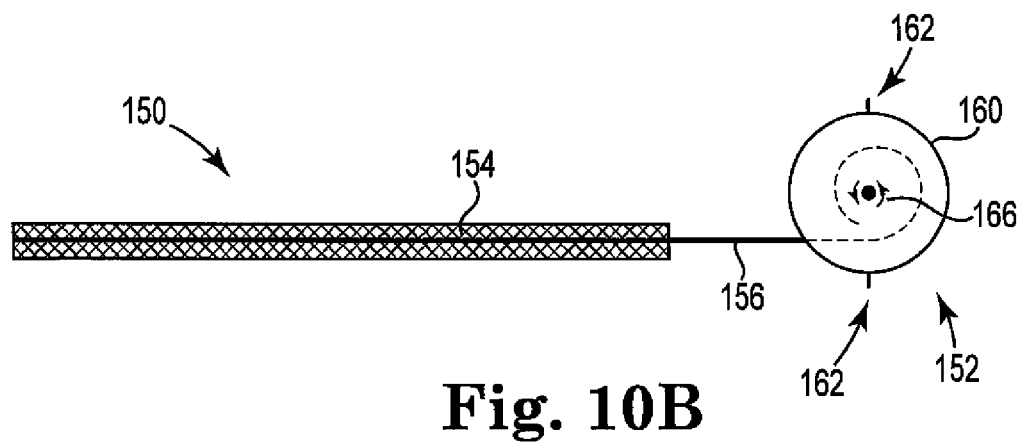

FIG. 10B shows an implant 150 similar to that of FIG. 10A, except that in this embodiment, a tensioning suture, wire, or other material 156 having a relatively small cross-section is attached to one end of mesh material 154, while the opposite end of the suture or other material is attached to adjusting mechanism 152. As with the system described at FIG. 10A, adjusting mechanism 152 can be actuated without invasive means, such as by using an external adjustment tool as described herein, or other mechanical, electronic, electromagnetic, or other communicative device. In this embodiment, as compared to the embodiment of FIG. 10A, motor housing 160 can be differently configured and sized due to the lower volume or "bulk" of a length of suture material 156 as compared to a similar length of a mesh material 154. It may be possible to use a smaller motor housing 160 when suture material 156 is being spooled or wound rather than when mesh material 154 is being wound with the motor housing. Motor housing 160 of the embodiment of FIG. 10B may be sized to accommodate only the winding of a length of suture material 156, or may be sized to accommodate both a length of suture and also a length of mesh material 154, such as if the implant cannot be adequately shortened only by winding the suture material 156 within housing 160.

Activation of adjusting mechanism 152 to reduce or increase a length of implant 150, by activating motor 160, may be performed in any useful manner. For example, an external tool can be inserted through the tissue (e.g., epidermis), i.e., through an incision, such as with a device (e.g., a needle) that allows for minimally invasive entry into the area of the body in which an adjusting mechanism. In this way, engagement of an internal adjusting mechanism can be accomplished by inserting the adjustment tool through the skin and into the patient, and can include smooth surfaces such as hemispheres or other curved surfaces that can engage through the skin with sufficient mechanical force to allow the external tool to engage and mechanically manipulate the internal adjusting mechanism. In another example, an adjusting mechanism can be activated externally from the patient's body, transcutaneously, through intact skin, thereby further minimizing patient trauma.

The patient may additionally or alternately be provided with a shunt-like access hole through the skin, which can allow the surgeon to have relatively easy access to an adjusting mechanism after the adjusting mechanism is implanted is placed subcutaneously in the patient. Such an access hole can be temporary or permanent, as desired. With this type of access, the system can include a spool that is implanted in the patient and a motor that is located outside the patient, wherein the motor is connected to the spool or other winding components within the patient via the access hole. The use of an external motor can thereby reduce the number of components that are implanted within a patient and minimize the corresponding bulk of the overall system. Attachment of the motor to the internally implanted components can be accomplished via electronic or mechanical connection of components.

An adjusting mechanism as described can be constructed of various biocompatible or biodegradable materials. A devices or device component can be made of any biologically safe material for implantation (tissue contact greater than 30 days), such as stainless steel, polycarbonate, polypropylene, PET, polyurethane, silicone, polysulphone, and Uitem, or the like, or combinations thereof. However, any suitable material is considered to be within the scope of the invention. For example, the motor housing can be made of a material that will eventually dissolve. Excess mesh (e.g., mesh that is wound within the motor housing) can eventually dissolve, thereby resulting in a lower volume of material remaining within the patient. Electrical power for a motor of an adjusting mechanism can be built up with a rechargeable system. With such a system, a battery can be relatively small and can optionally be rechargeable at some time after a surgical implantation procedure, such as at an office visit after the surgery is complete.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A combination comprising a pelvic implant and an adjusting tool, the combination useful to treat a pelvic condition,
    the implant comprising:
        a tissue support portion,
        a first extension portion extending from a proximal end connected to the tissue support portion to a distal end,
        a second extension portion extending from a proximal end connected to the tissue support portion to a distal end,
        a first adjusting mechanism at the distal end of the first extension portion, and
        a second adjusting mechanism at the distal end of the second extension portion,
    wherein the implant has a length to allow the first adjusting mechanism and the second adjusting mechanism to each be placed subcutaneously in a patient at a location adjacent the patient's epidermis with the central support portion supporting tissue of a urethra or an anus,
    wherein the first adjusting mechanism is adapted to rotate to reduce a length of the first extension portion, and
    wherein the second adjusting mechanism is adapted to rotate to reduce a length of the second extension portion, the adjusting tool comprising a surface capable of engaging the first adjusting mechanism or the second adjusting while the first or second adjusting mechanism is implanted subcutaneously in the patient adjacent the patient's epidermis.

2. A combination as recited at claim 1 wherein the implant comprises supportive portions consisting of the central support portion and the two extension portions.

3. A combination as recited at claim 1 wherein the first and second extension portions have lengths to passthrough opposing obturator foramen.

4. A combination as recited at claim 1 wherein the first and second extension portions have lengths to pass behind a pubic symphysis.

5. A combination as recited at claim 1 wherein the adjusting tool is capable of engaging the adjusting mechanism transcutaneously through a patient's intact skin, while the adjusting mechanism is implanted subcutaneously in a patient.

6. A combination as recited at claim 1 wherein the adjusting tool is capable of engaging the adjusting mechanism percutaneously through an incision in a patient's skin, while the adjusting mechanism is implanted subcutaneously in a patient.

7. A combination as recited at claim 1 wherein the adjusting mechanism comprises a motor.

8. A combination as recited at claim 5 wherein the adjusting tool comprises a moveable surface selected from the group consisting of: a plurality of hemi-spheres and a blade, the moveable surface being capable of being rotated against a surface of a patient's skin without damaging the skin.

9. A method of treating a pelvic condition, the method comprising
providing a pelvic implant useful to treat a pelvic condition, the implant comprising:
a tissue support portion,
a first extension portion extending from a proximal end connected to the tissue support portion to a distal end,
a second extension portion extending from a proximal end connected to the tissue support portion and a distal end, and
a first adjusting mechanism at the distal end of the first extension portion, and
a second adjusting mechanism at the distal end of the second extension portion,
wherein the implant has a length to allow the first adjusting mechanism and the second adjusting mechanism to each be placed subcutaneously in a patient at a location adjacent the patient's epidermis with the central support portion supporting tissue of a urethra or an anus,
wherein the first adjusting mechanism is adapted to rotate to reduce a length of the first extension portion, and
wherein the second adjusting mechanism is adapted to rotate to reduce a length of the second extension portion,
providing an adjusting tool capable of engaging the first adjusting mechanism or the second adjusting mechanism while the first or second adjusting mechanism is implanted subcutaneously in a patient at a location adjacent the patient's epidermis,
placing the implant in the patient to support tissue of the urethra with the first and second adjusting mechanisms located subcutaneously adjacent the patient's epidermis, and
post-operatively engaging the adjusting tool with the first or second adjusting mechanism to actuate the first or second adjusting mechanism and adjust a length of the first extension portion or a length of the second extension portion.

10. A method as recited at claim 9 wherein the adjusting tool engages the adjusting mechanism transcutaneously through intact skin of the patient.

11. A method as recited at claim 9 wherein the adjusting tool engages the adjusting mechanism percutaneously through an incision in the skin of the patient.

12. A method as recited at claim 9 comprising adjusting the length of the first extension portion and the length of the second extension portion together to prevent supported tissue from being moved in a left or a right direction within the patient.

13. A method as recited at claim 10 wherein the pelvic condition is selected from the group consisting of: fecal incontinence, urinary incontinence, and vaginal prolapse.

14. A method as recited at claim 13 for treating urinary incontinence, the method comprising:
creating a medial incision in the patient,
placing the tissue support portion to contact tissue to support the urethra,
placing the first extension portion in a tissue path extending through a first obturator foramen of the patient,
placing the second extension portion in a tissue path extending through a second obturator foramen of the patient,
placing the first adjusting mechanism at a subcutaneous location adjacent the patient's epidermis,
placing the second adjusting mechanism at a subcutaneous location adjacent the patient's epidermis, and
closing the medial incision.

15. A method according to claim 14 comprising adjusting the length of the extension portion at a time in a range from 1 day to 3 weeks after closing the medial incision.

16. A method according to claim 9 for treating vaginal vault prolapse, the method comprising
placing the tissue support portion in the patient to support tissue of a vaginal vault, and
placing the adjusting mechanism in the patient subcutaneously at a location near a sacrum.

17. A method according to claim 16 comprising adjusting the length of the extension portion at a time in a range from 1 day to 3 weeks after closing the medial incision.

18. A combination as recited at claim 5 wherein the adjusting tool communicates with the adjusting mechanism by a mechanical engagement, magnetic engagement, or an electromagnetic engagement.

19. A combination as recited at claim 6 wherein the adjusting tool communicates with the adjusting mechanism by a frictional engagement or a magnetic engagement.

* * * * *